United States Patent
Hager

(10) Patent No.: US 9,500,595 B2
(45) Date of Patent: Nov. 22, 2016

(54) METHODS FOR ENHANCED GRADING OF MINT QUALITY COINS

(71) Applicant: M.A.C.GE, LLC, Lake Monroe, FL (US)

(72) Inventor: Charles Alan Hager, Sanford, FL (US)

(73) Assignee: M.A.C.GE, LLC, Lake Monroe, FL (US)

( * ) Notice: Subject to any disclaimer, the term of this patent is extended or adjusted under 35 U.S.C. 154(b) by 77 days.

(21) Appl. No.: 14/583,394

(22) Filed: Dec. 26, 2014

(65) Prior Publication Data

US 2016/0187261 A1    Jun. 30, 2016

(51) Int. Cl.
*G01N 21/88* (2006.01)
*G07D 5/00* (2006.01)

(52) U.S. Cl.
CPC .......... *G01N 21/8803* (2013.01); *G07D 5/005* (2013.01)

(58) Field of Classification Search
None
See application file for complete search history.

(56) References Cited

U.S. PATENT DOCUMENTS

| | | | | |
|---|---|---|---|---|
| 3,349,612 | A * | 10/1967 | Sherman | G01N 3/56 33/542 |
| 4,124,111 | A * | 11/1978 | Hayashi | G07D 5/08 194/319 |
| 8,661,889 | B2 | 3/2014 | Blake | |
| 2003/0102197 | A1* | 6/2003 | Furuya | G07D 5/005 194/318 |
| 2005/0011772 | A1* | 1/2005 | Eichenbaum | A45C 1/06 206/0.8 |
| 2008/0023351 | A1* | 1/2008 | Macor | B65D 85/58 206/232 |
| 2011/0126618 | A1* | 6/2011 | Blake | G07D 5/005 73/163 |
| 2015/0131890 | A1* | 5/2015 | Rourk | G06T 7/001 382/136 |

FOREIGN PATENT DOCUMENTS

| | | | | |
|---|---|---|---|---|
| DE | 10039658 A1 * | 2/2002 | | G06Q 20/32 |
| DE | 10039659 A1 * | 2/2002 | | G07D 5/00 |
| EP | 0328441 A2 * | 8/1989 | | G07D 5/08 |
| JP | 2000268221 A * | 9/2000 | | |
| JP | 2001167311 A * | 6/2001 | | |

\* cited by examiner

*Primary Examiner* — Andre Allen
(74) *Attorney, Agent, or Firm* — Gordon & Jacobson, P.C.

(57) ABSTRACT

Grade enhancement of mint grade and proof-like coins is disclosed based on a determination of an indication that the coin was a "first strike" coin. First strike is defined by the first 10% or less of coins struck by the same die and may be determined by the location of a physical attribute of the coin present in at most 10% of similar coins struck by the same die. First strike in proof-like coins may be determined by frosted white cameo.

20 Claims, 6 Drawing Sheets

  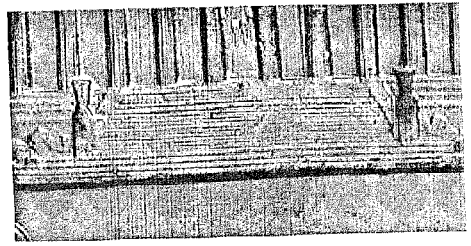
FIG. 2a  FIG. 2b  FIG. 2c
  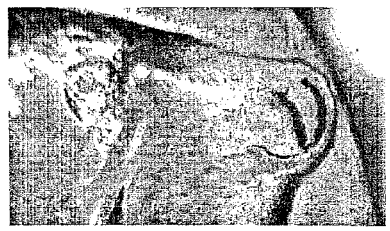
FIG. 3a  FIG. 3b  FIG. 3c
  
FIG. 4a  FIG. 4b  FIG. 4c

  
FIG. 9a    FIG. 9b    FIG. 9c
 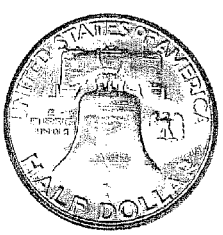 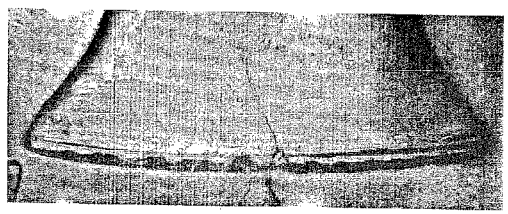
FIG. 10a    FIG. 10b    FIG. 10c
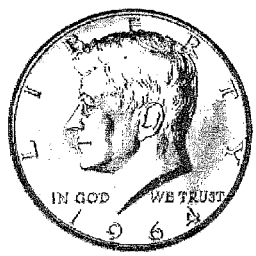  
FIG. 11a    FIG. 11b    FIG. 11c

METHODS FOR ENHANCED GRADING OF MINT QUALITY COINS

BACKGROUND OF THE INVENTION

1. Field

The present disclosure relates to numismatic assessment of coin quality. More particularly, the present disclosure relates to methods for grade enhancing mint state coins.

2. State of the Art

In 1949, Dr. William H. Sheldon presented a scale for grading coins. The scale, known as the Sheldon Scale has a seventy-point range including a subset of grades for circulated coins and a subset for uncirculated coins. The circulated coin scaling runs from a grade of 1 (poor) to a grade of 59 (choice, about uncirculated with almost all of the original mint luster remaining), and includes grades such as fair (2), about good (3), good (4), very good (8), fine (12), very fine (20), extremely fine (40), about uncirculated (50), as well as other grades in-between. The uncirculated grade scaling (60-70) are for coins which are called "mint state" or "as new" coins. In the Sheldon Scale, the mint state coins are differentiated by eye appeal, luster, wear, scratches, and hairlines. Thus, a mint state 60 may be considered unattractive, dull or have a washed out luster with hairlines, unattractive large areas of scuff-marks with rim nicks, while a mint state 64 might have average luster and strike with small contact marks in groups as well as one or two moderately heavy marks, one or two small patches of hairlines under low magnification, noticeable light scuff marks or defects, and pleasing eye appeal. A mint state 70, on the other hand, is considered a perfect coin with no trace of wear, handling, scratches or contact with other coins and exceptional eye appeal. Other mint grades in the mint grade subset fall between the extremes.

Recently, some numismatists have started providing an enhanced grade to certain mint state coins. For example, U.S. Pat. No. 8,551,889 to Blake discloses providing an eye appeal indicator symbol (+) adjoining a coin's Sheldon whole number grade on a label attached to a clear plastic coin holder in order to enhance the value of the coin by providing an above-average fractional grade condition for the coin. The eye appeal indicator is based on using determining one or more "axial ultimate refractory angles" (AU-RAs) of a coin that effectively measure the maximum surface reflectivity of the coin.

While enhanced grades based on eye appeal may be used as a mechanism to attempt to distinguish amongst coins of a single grade, eye appeal, even using surface reflectivity, is an artificial grading. When coins that may be one Sheldon Scale grade apart can sell for a difference on the order of a hundred or even a thousand times the price, an enhanced grading based on an artificial grading mechanism is not particularly desirable.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one embodiment, enhanced grading of a mint state coin is based on a determinable structural aspect of the mint state coin resulting from a "first strike" of a die and found on only a small percentage of coins in a particular Sheldon Scale mint state grade.

In one aspect, a "first strike" is defined as a strike made early in the run of a die which is reflected in a physical attribute of the resulting coin such that at most 10% of coins struck on that die have that physical attribute. In older or "traditional" coins (defined as struck prior to 1960), typically less than 2% of coins were struck with a first strike such that they retain particular physical attributes as described in more detail below. In some cases, such as during war time when more coins were struck with each die, less than 1% of the coins struck by a die were struck with a first strike. In modern coins (struck in 1960 and thereafter), only up to 10% of the coins struck are struck with a first strike.

In one embodiment, a first strike of a mint coin is revealed by the detail provided by the device of the die seen on the resulting coin.

In one embodiment specific to proof-like coins where a die is polished with diamond dust prior to striking of coins, a first strike of a mint coin is revealed by the cameo of the coin resulting from the strike.

Multiple examples of a determinable structural aspect resulting from a first strike coin are provided. Examples include, among others: the presence of four bottom steps separated by a line on the Lincoln Memorial on the reverse of the Lincoln cent (1958 to 2008); a full spread of the end of the tail tassels of the buffalo on the reverse of the Buffalo Nickel (1913 to 1938); four fully separated steps or at least 90% separation of five steps of the Jefferson Memorial Steps on the reverse of the Jefferson nickel (1938 to present); a torch with full bands at the top and 90% of the bands and cross bands in the middle and bottom of the torch on the reverse of the Mercury dime (1916 to 1945); 90% of Lady Liberty's head and hair braids visible on the front of the Standing Liberty quarter (1916 to 1930); an eagle's beak with 50% of the top and bottom of the beak separated and defined on the reverse of a Washington quarter (1932 to 1998); a Lady Liberty right arm extending down across her waistline with her hand and thumb defined around the wreath stems with the thumb having separation from the hand and the wheat line through the hand defined on the obverse of a Walking Liberty half dollar (1916 to 1947); a Morgan dollar between (1878 to 1921), Sheldon Scale 64 (or higher), where the obverse provides detail of Lady Liberty's ear and hair curls over and around the ear having depth, and the reverse provides visible breast feathers; and a Peace Dollar (1921-1935), Sheldon Scale 64 (or higher), where the obverse provides sharp hair detail from Lady Liberty's crown along her face and past the nape of her neck and the reverse provides distinct layers of wing feathers and distinct feather in the wing layers and tail. In each case, the presence of the defined structural aspects of the mint coin are indicative of a high pressure strike that structurally distinguishes the coin from at least 90% of all similar coins struck on the same die, thereby rendering the coin more rare and valuable.

Additional objects and advantages will become apparent to those skilled in the art upon reference to the detailed description taken in conjunction with the provided figures.

BRIEF DESCRIPTION OF THE DRAWINGS

FIGS. 2a, 2b, and 2c are respectively magnified photographs of the front (obverse) and back (reverse) of a first mint state Lincoln Memorial cent, and a highly magnified photograph of a portion of the reverse of a similar coin.

FIGS. 3a, 3b, and 3c are respectively magnified photographs of the front and back of a first mint state Buffalo nickel, and a highly magnified photograph of a portion of the reverse of a similar mint state Buffalo nickel.

FIGS. 4a, 4b, and 4c are respectively magnified photographs of the front and back of a first mint state Jefferson nickel, and a highly magnified photograph of a portion of the reverse of a similar coin.

FIGS. 9a, 9b, and 9c are respectively magnified photographs of the front and back of a first mint state Walking Liberty half dollar, and a highly magnified photograph of a portion of the obverse of a similar coin.

FIGS. 10a, 10b, and 10c are respectively magnified photographs of the front and back of a first mint state Franklin half dollar, and a highly magnified photograph of a portion of the reverse of a similar coin.

FIGS. 11a, 11b, and 11c are respectively magnified photographs of the front and back of a first mint state Kennedy half dollar, and a highly magnified photograph of a portion of the reverse of a similar coin.

DETAILED DESCRIPTION

In 1985, Alan Hager, the inventor hereof, invented coin slabbing where graded coins were encapsulated in a plastic holder that incorporates a certificate attesting to the grade of the coin. Since then, over 50 million coins have been slabbed.

Figure 1B:
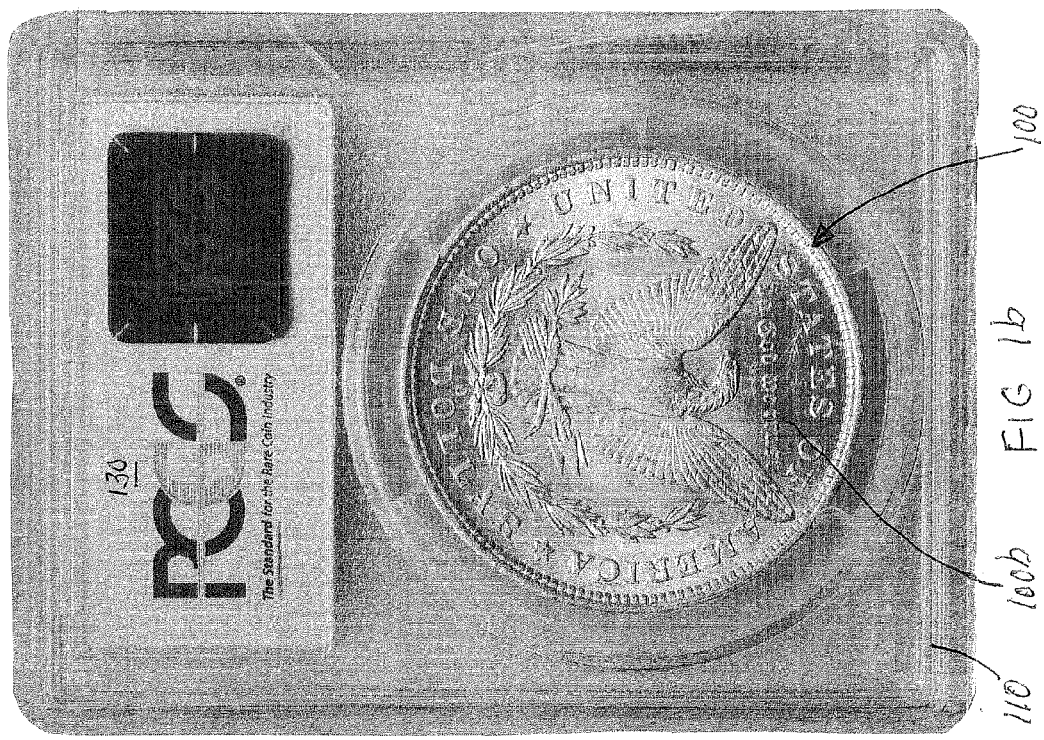
FIGS. 1a and 1b are schematic drawings showing the front and back of a coin holder (slab) holding a certified Sheldon Scale graded coin with enhanced grading.
Figure 1A:
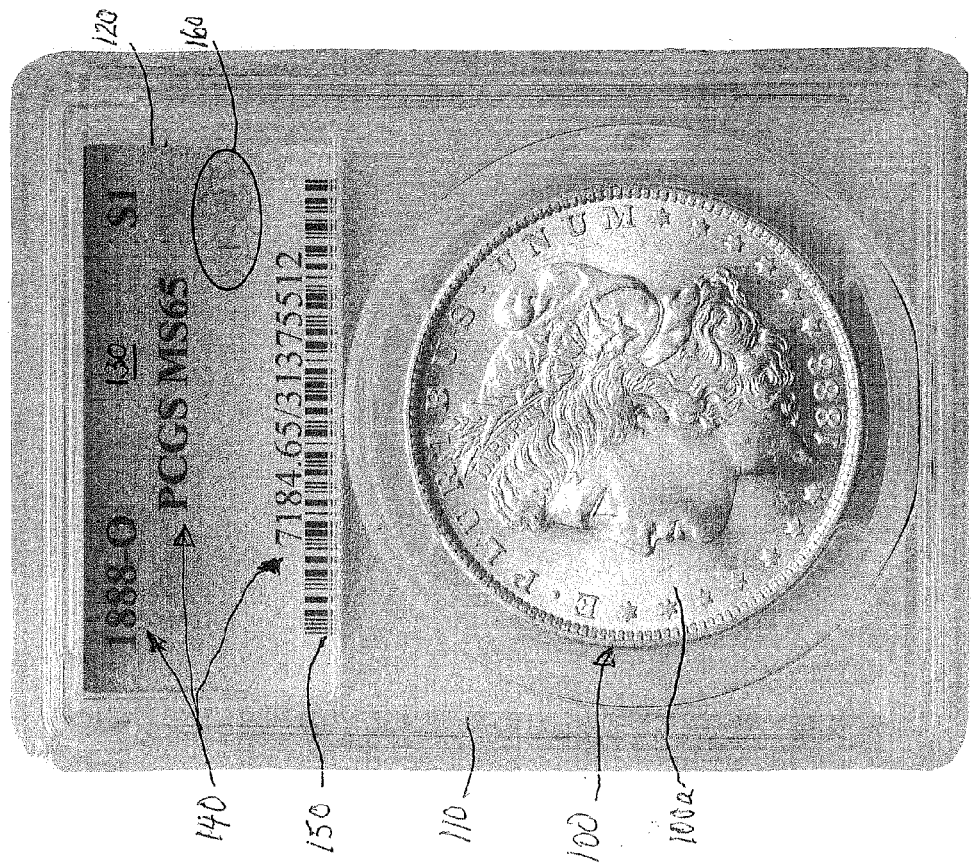

FIGS. 1a and 1b are schematics of a coin that has been certified, slabbed and then subject to grade enhancement as described in more detail hereinafter. In particular, in FIG. 1a, the obverse 100a of a mint grade coin 100 is seen encapsulated in a plastic holder 110. The reverse 100b of the coin 100 is seen in FIG. 1b. As seen in FIG. 1a, the plastic holder also includes a compartment 120 for a certificate 130. The certificate typically contains information 140 regarding the coin, its mint state Sheldon Grade, and the name of the certifier. A bar code 150 that uniquely identifies the coin may also be provided. A grade enhancement hologram 160 is shown attached on the outside of the holder 110. As will be described in more detail hereinafter, the grade enhancement indicator 160 certifies that the mint state coin located in the holder 110 contains a determinable structural aspect resulting from a first strike that is found on only a small percentage of coins in a particular Sheldon Scale grade. As such, the coin is granted a grade enhancement indicated by a plus (+) or star (*) or other grade enhancement indicator (such as FS (first strike)) which should enhance the value of the coin relative to similar coins of the same Sheldon Grade that were not minted with a first strike. In one embodiment, the grade enhancement indicator may include an indication of the source of grade enhancement.

In one embodiment, a method for the grade enhancement of a mint state coin includes: (i) inspecting the mint state coin to either provide a Sheldon grade, to confirm the Sheldon grade, or to confirm that a Sheldon grade certification exists for the mint state coin, (ii) inspecting at least one of the obverse and the reverse of the mint state coin, (iii) determining, e.g., from the inspecting, whether the mint state coin is a first strike coin, and (iv) providing a grade enhancement indicator for the mint state coin only if the mint state coin is a first strike coin. In one embodiment, the grade enhancement indicator is provided by generating a hologram and affixing the hologram to a slab containing the coin. In one embodiment, the grade enhancement indicator is provided by generating a sticker with a grade enhancement indicator and affixing the sticker to a slab containing the coin.

Turning to FIGS. 2a and 2b, the front (obverse) and back (reverse) of a first mint state U.S. Lincoln Memorial 2002 cent struck in Denver (D), with FIG. 2c showing a highly magnified photograph of the step portion of the reverse of a similar coin. In one embodiment, a first strike is revealed in a Lincoln Memorial mint state cent 1958 to 2008 where the steps of the Lincoln Memorial on the reverse show visible top and bottom steps with the four bottom steps being separated by a complete line, e.g., as seen in FIG. 2c.

In FIGS. 3a and 3b, the front and back of a first mint state U.S. Buffalo 1913 Nickel are shown, with FIG. 3c showing a highly magnified photograph of a hind/tail portion of the reverse of a similar coin. In one embodiment, a first strike is revealed in a Buffalo mint state nickel 1913 to 1938 where the tail of the buffalo on the reverse exhibits a full spread (90% to 100%) of the end of the tail tassels, e.g., as seen in FIG. 3c.

FIGS. 4a and 4b show the front and back of a first mint state U.S. Jefferson nickel 1947 struck in San Francisco (S), and FIG. 4c shows a highly magnified photograph of the step portion of Monticello on the reverse of a similar coin. In one embodiment, a first strike is revealed in a Jefferson mint state nickel 1938 and later (to at least 2015) where, on the reverse, starting from the top of the steps of Monticello and proceeding downward from step one to step four, the steps are separated with a full (100%) step line, e.g., as seen in FIG. 4c. In another embodiment, a first strike is revealed in a U.S. Jefferson mint state nickel 1938 to 2015 where, on the reverse, starting from the top of the steps of Monticello and proceeding downward from step one to step five, at least 80% of the five steps are visible.

Figure 5A:
FIGS. 5a, 5b, and 5c are respectively magnified photographs of the front and back of a mint state Mercury dime, and a highly magnified photograph of a portion of the reverse of a similar coin.
Figure 5B:
Figure 5C:
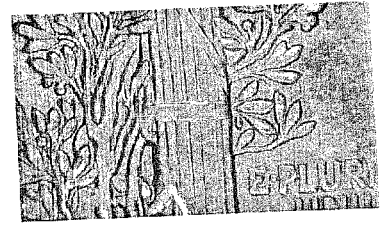

FIGS. 5a and 5b show the front and back of a first mint state U.S. Mercury dime 1916 struck at West Point (W), and FIG. 5c shows a highly magnified photograph of a portion of the torch on the reverse of a similar coin. In one embodiment, a first strike is revealed in a Mercury mint state dime 1916 to 1945 where, on the reverse, the torch exhibits three full bands at the top and two full bands in the middle and bottom of the torch. The three sets of bands must be well defined and separated in the center by a line that is at least 90% complete, e.g., as seen in FIG. 5c.

Figure 6A:
FIGS. 6a, 6b, and 6c are respectively magnified photographs of the front and back of a first mint state Roosevelt dime, and a highly magnified photograph of a portion of the reverse of a similar coin.
Figure 6B:
Figure 6C:

FIGS. 6a and 6b show the front and back of a first mint state U.S. Roosevelt dime 1996 struck at West Point (W), and FIG. 6c shows a highly magnified photograph of a portion of the torch on the reverse of a similar coin. In one embodiment, a first strike is revealed in a Roosevelt mint state dime 1946 and later (to at least 2015) where, on the reverse, the torch exhibits full separate bands at the top (i.e., separated by a full line) and separate bands at the bottom of the torch with at least a line extending 90% of the way across, with weakness at the ends of the bottom bands only, e.g., as seen in FIG. 6c.

Figure 7A:
FIGS. 7a, 7b, and 7c are respectively magnified photographs of the front and back of a first mint state Standing Liberty quarter, and a highly magnified photograph of a portion of the obverse of a similar coin.
Figure 7B:
Figure 7C:

FIGS. 7a and 7b show the front and back of a first mint state U.S. Standing Liberty quarter 1917, and FIG. 7c shows a highly magnified photograph of a portion of the obverse of a similar coin. In one embodiment, a first strike is revealed in a Standing Liberty mint state quarter 1916 to 1930 where, on the obverse, on Lady Liberty's head, a line is visible between the forehead and the hair bangs, weakness is exhibited between the hair braids and the right cheekbone, and at least 90% of the hair braids are well defined, e.g., as seen in FIG. 7c.

Figure 8A:
FIGS. 8a, 8b, and 8c are respectively magnified photographs of the front and back of a first mint state Washington quarter, and a highly magnified photograph of a portion of the reverse of a similar coin.
Figure 8B:
Figure 8C:
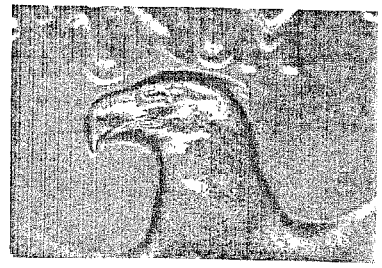

FIGS. 8a and 8b show the front and back of a first mint state U.S. Washington quarter 1932, and FIG. 8c shows a highly magnified photograph of a portion of the reverse of a similar coin. In one embodiment, a first strike is revealed in a Washington mint state quarter 1932 to 1998, where on the reverse, the eagle's beak has the top and bottom beak separated and defined at least 50% along the length of the beak, e.g., as seen in FIG. 8c.

FIGS. 9a and 9b show the front and back of a first mint state U.S. Walking Liberty half dollar 1921, and FIG. 9c shows a highly magnified photograph of a portion of the obverse of a similar coin. In one embodiment, a first strike is revealed in a Walking Liberty mint state half dollar 1916 to 1947, where on the reverse, the left arm of Lady Liberty extends down across her waistline with her hand and thumb defined around the steams of a wreath. The thumb must have separation from the hand. The wheat line through the hand should be defined, e.g., as seen in FIG. 9c.

FIGS. 10a and 10b show the front and back of a first mint state U.S. Franklin half dollar 1953, and FIG. 10c shows a highly magnified photograph of a portion of the reverse of a similar coin. In one embodiment, a first strike is revealed in a Franklin mint state half dollar 1948 to 1963 where on the reverse, the bottom of the Liberty bell includes two sets of three bell lines, where the upper bell lines are complete except for the interruption of the Liberty bell crack, and the bottom three lines have at least 90% separation (i.e., no more than 10% of any line is missing), e.g., as seen in FIG. 10c.

FIGS. 11a and 11b show the front and back of a first mint state U.S. Kennedy half dollar 1964, and FIG. 11c shows a highly magnified photograph of a portion of the reverse of a similar coin. In one embodiment, a first strike is revealed in a Kennedy mint state half dollar 1964 and later (to at least 2015) where on the reverse, the bottom and top of the eagle's beak has full separation and definition. The separation must be from top to bottom of the beak and running from left to right until the separation ends at the snake in the eagle's beak, and continuing on the right side of the snake to the end of the beak, e.g., as seen in FIG. 11c.

Figure 12A:
FIGS. 12a and 12b are respectively magnified photographs of the front and back of a Morgan dollar with an "O" strike indication.
Figure 12B:

FIGS. 12a and 12b are respectively magnified photographs of the front and back of a mint state U.S. Morgan dollar 1880 struck in New Orleans (O). In one embodiment, a first strike is revealed in a Morgan dollar from 1878 to 1921 having a Sheldon Scale 64 (or higher), where the obverse provides detail of Lady Liberty's ear with hair curls over and around the ear having depth, e.g., as seen in FIG. 12a, and the reverse provides visible breast feathers, e.g., as seen in FIG. 12b.

Figure 13B:
FIGS. 13a and 13b are respectively magnified photographs of the front and back of a Peace dollar with an "S" strike indication.
Figure 13A:

FIGS. 13a and 13b are respectively magnified photographs of the front and back of a mint state U.S. Peace dollar 1925 struck in San Francisco (S). In one embodiment, a first strike is revealed in a Peace mint state dollar 1921 to 1935 struck in having a Sheldon Scale 64 or higher, where the obverse provides details of Lady Liberty's hair from the crown along her face and past the nape of her neck, e.g., as seen in FIG. 13a, and the reverse provides three distinct layers of wing feathers and tail layer with distinct feathers in the wing layers and tail, e.g., as seen in FIG. 13b.

In one embodiment specific to proof-like coins, where a die is polished with diamond dust prior to striking of coins, a first strike of a mint coin is revealed by the cameo or shine of the coin resulting from the strike. In one aspect, in the minting of these proof-like coins, the diamond dust polish disappears quickly resulting in a different look of subsequently minted proof-like coins.

Figure 14B:
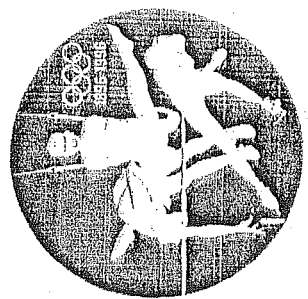
FIGS. 14a and 14b are respectively magnified photographs of the front and back of a Canadian fifteen dollar Elizabeth II proof-like coin having ultra heavy cameo.
Figure 14A:

More particularly, and turning to FIGS. 14a and 14b, magnified photographs of the front and back of a Canadian fifteen dollar Elizabeth II proof-like coin is seen. In one embodiment, a first strike is revealed in U.S. or foreign proof coins where the devices (details), lettering, fascia, and raised areas of the coin exhibit full frosted white cameo raised areas reflecting against a mirror surface contrast to provide an ultra heavy cameo. The coin of FIGS. 14a and 14b is suggests a first strike that would occur in the first 2% of proof-like coins struck by a single die.

Figure 15B:
FIGS. 15a and 15b are respectively magnified photographs of the front and back of an Eisenhower presidential dollar proof-like coin having heavy cameo.
Figure 15A:

FIGS. 15a and 15b are respectively magnified photographs of the front and back of a bicentennial Eisenhower presidential dollar proof-like coin. In one embodiment, a first strike is revealed in U.S. and foreign proof-like coins where the devices, lettering, fascia and raised areas of the coin exhibit frosted white raised areas to provide a heavy cameo. The coin of FIGS. 15a and 15b suggests a first strike that would occur in the first 10% of proof-like coins struck by a single die, as it does not have the same level of whiteness or cameo as the coin of FIGS. 14a and 14b, and the background does not provide a mirror surface contrast.

There have been described and illustrated herein several embodiments of a method of grade enhancing a coin. While particular embodiments have been described, it is not intended that the invention be limited thereto, as it is intended that the invention be as broad in scope as the art will allow and that the specification be read likewise. Thus, while grade enhancement based on first strike for particular coins have been disclosed, it will be appreciated that first strike determinations may be made for other coins as well. Also, while first strike of U.S. coins based on a physical attribute of the resulting coin such that at most 10% of coins struck on that die have that physical attribute has been described, it will be appreciated that first strike of certain foreign coins may be similarly determined. It will therefore be appreciated by those skilled in the art that yet other modifications could be made to the provided invention without deviating from its spirit and scope as claimed.

What is claimed is:

1. A method for grade enhancement of a mint state coin, comprising:

inspecting the mint state coin to either provide a Sheldon grade, to confirm a previously granted Sheldon grade, or to confirm that a Sheldon grade certification exists for the mint state coin;

inspecting at least one of the obverse and the reverse of the mint state coin;

determining whether the mint state coin is a first strike coin; and affixing a sticker on a slab containing the mint state coin and indicating a grade enhancement for the mint state coin only if the mint state coin is a first strike coin.

2. A method according to claim 1, wherein:

the mint state coin is a U.S. Lincoln cent 1958 to 2008, said inspecting comprises inspecting the reverse of the U.S. Lincoln cent 1958 to 2008 having an image of the Lincoln Memorial, and said determining comprises determining whether the steps of the Lincoln Memorial on the reverse of the Lincoln cent show visible top and bottom steps with the four bottom steps being separated by complete lines.

3. A method according to claim 1, wherein:

the mint state coin is a U.S. Buffalo nickel 1913 to 1938, said inspecting comprises inspecting the reverse of the U.S. Buffalo nickel 1913 to 1938 having an image of a buffalo with a tail, and said determining comprises determining whether the tail of the buffalo on the reverse exhibits a full spread (90% to 100%) of the end of the tail tassels.

4. A method according to claim 1, wherein:

the mint state coin is a U.S. Jefferson nickel 1938 or later, said inspecting comprises inspecting the reverse of the U.S. Jefferson nickel 1938 or later having an image of Monticello, and said determining comprises determining whether the top four steps of Monticello on the reverse are separated with a full step line.

5. A method according to claim 1, wherein:

the mint state coin is U.S. Jefferson nickel 1938 or later, said inspecting comprises inspecting the reverse of the U.S. Jefferson nickel 1938 or later having an image of Monticello, and said determining comprises determining whether 80% of the five steps of Monticello on the reverse are visible.

6. A method according to claim 1, wherein:

the mint state coin is a U.S. Mercury dime 1916 to 1945, said inspecting comprises inspecting the reverse of the U.S. Mercury dime 1916 to 1945 having an image of a torch, and said determining comprises determining whether the torch on the reverse exhibits three full bands at the top and two full bands in the middle and bottom of the torch where the three sets of bands are well defined and separated in the center by a line that is at least 90% complete.

7. A method according to claim 1, wherein:

the mint state coin is a Roosevelt dime 1946 or later, said inspecting comprises inspecting the reverse of the Roosevelt dime 1946 or later having an image of a torch, and said determining comprises determining whether the torch exhibits full separate bands toward the top or the torch and substantially separate bands at the bottom of the torch such that a line extends at least 90% across, with weakness at the ends of the bottom bands only.

8. A method according to claim 1, wherein:

the mint state coin is a U.S. Standing Liberty quarter 1916 to 1930, said inspecting comprises inspecting the obverse of the U.S. Standing Liberty quarter 1916 to 1930 having an image of Lady Liberty with a head, a cheekbone, and hair bangs and braids, and said determining comprises determining whether a line is visible between the forehead and the hair bangs of Lady Liberty, weakness is exhibited between the hair braids and the right cheekbone, and at least 90% of the hair braids are well defined.

9. A method according to claim 1, wherein:

the mint state coin is a U.S. Washington quarter 1932 to 1998, said inspecting comprises inspecting the reverse of the U.S. Washington quarter 1932 to 1998 having an image of an eagle with a beak, and said determining comprises determining whether the eagle's beak has the top and bottom beak separated and defined at least 50% along the length of the beak.

10. A method according to claim 1, wherein:

the mint state coin is a U.S. Walking Liberty half dollar 1916 to 1947, said inspecting comprises inspecting the obverse of the U.S. Walking Liberty half dollar 1916 to 1947 having an image of Lady Liberty with her left hand holding wreath stems, and said determining comprises determining whether the thumb on Lady Liberty's left hand is separated from the hand with the hand extending around the steams of a wreath.

11. A method according to claim 1, wherein:

the mint state coin is a U.S. Franklin half dollar 1948 to 1963, said inspecting comprises inspecting the reverse of the U.S. Franklin half dollar 1948 to 1963 having an image of the Liberty Bell, and said determining comprises determining whether the bottom of the Liberty bell includes two sets of three bell lines, where the upper bell lines are complete except for the interruption of the Liberty bell crack, and the bottom three bell lines have at least 90% separation.

12. A method according to claim 1, wherein:

the mint state coin is a U.S. Kennedy half dollar 1964 or later, said inspecting comprises inspecting the reverse of the U.S. Kennedy half dollar 1964 or later having an image of an eagle with a snake in its beak, and said determining comprises determining whether the bottom and top of the eagle's beak has full separation and definition with the separation being between the top to bottom of the beak and running from left to right until the separation ends at the snake in the eagle's beak and continuing on the right side of the snake to the end of the beak.

13. A method according to claim 1, wherein:

the mint state coin is U.S. Morgan dollar 1878 to 1921 grade MS64 or better, said inspecting comprises inspecting the obverse and reverse of the U.S. Morgan dollar 1878 to 1921 grade MS64 or better, the obverse having an image of the head of Lady Liberty with an ear and hair, and the reverse having an image of a spread-wing eagle, said determining comprises determining whether detail of Lady Liberty's ear is visible with hair curls over and around the ear having depth, and whether the eagle has visible individual breast feathers.

14. A method according to claim 1, wherein:
the mint state coin is U.S. Peace dollar 1921 to 1935 grade MS64 or better,
said inspecting comprises inspecting the reverse the obverse and reverse of the U.S. Peace dollar 1921 to 1935 grade MS64 or better, the obverse having an image of the head of Lady Liberty with a crown, face, hair and neck, and the obverse having an eagle with folded wings and a tail,
said determining comprises determining whether the obverse provides details of Lady Liberty's hair from the crown, along her face and past the nape of her neck, and the reverse provides three distinct layers of wing feathers and a tail layer, and said three distinct layers of wing feathers and said tail layer each have distinct feathers shown.

15. A method according to claim 1, wherein:
said providing comprises attaching a grade enhancement indication to a holder holding the coin.

16. A method for grade enhancement of a proof-like coin, comprising:
inspecting the proof coin to either provide a Sheldon grade, to confirm a previously granted Sheldon grade, or to confirm that a Sheldon grade certification exists for the proof-like coin;
inspecting both the obverse and the reverse of the proof-like coin;
determining whether the proof-like coin is a first strike coin; and
affixing a sticker on a slab containing the proof-like coin and indicating a grade enhancement for the proof-like coin only if the proof-like coin is a first strike coin.

17. A method according to claim 16, wherein:
said determining comprises determining whether all devices, lettering, fascia and raised areas on the obverse and reverse of the coin exhibit full frosted white cameo with the full frosted white cameo reflecting against a mirror surface contrast to provide an ultra heavy cameo contrast.

18. A method according to claim 16, wherein:
said determining comprises determining whether all devices, lettering, fascia and raised areas on the obverse and reverse of the coin exhibit frosted white cameo.

19. A method for grade enhancement of a coin, comprising:
inspecting the coin to either provide a Sheldon grade of at least 60, to confirm a previously granted Sheldon grade of at least 60, or to confirm that a Sheldon grade certification of at least 60 exists for the mint state or proof-like coin;
inspecting at least one of the obverse and the reverse of the coin to determine whether or not a physical attribute present in at most 10% of like coins is present in the inspected coin; and
affixing a sticker on a slab containing the coin and indicating a grade enhancement for the coin if the physical attribute is present.

20. A method according to claim 19, wherein:
the coin is a proof-like coin and said inspecting comprises inspecting both the obverse and reverse of the proof-like coin.

* * * * *